United States Patent [19]

Inglett

[11] Patent Number: 5,225,219
[45] Date of Patent: Jul. 6, 1993

[54] AMYLODEXTRIN COMPOSITIONS AND METHOD THEREFOR

[75] Inventor: George E. Inglett, Peoria, Ill.

[73] Assignee: The United States of America, as represented by the Secretary of Agriculture, Washington, D.C.

[21] Appl. No.: 815,996

[22] Filed: Jan. 2, 1992

[51] Int. Cl.$^5$ .......................... A23L 1/105; A23L 1/09
[52] U.S. Cl. .......................................... 426/28; 426/44; 426/46; 426/49; 426/650; 435/94; 435/96; 435/99
[58] Field of Search ....................... 426/28, 44, 46, 49, 426/650, 661; 435/94, 98, 99

[56] References Cited

U.S. PATENT DOCUMENTS

| | | | |
|---|---|---|---|
| 3,640,729 | 2/1972 | Ronai et al. | 99/83 |
| 3,663,369 | 5/1972 | Morehouse et al. | 195/31 |
| 4,282,319 | 8/1981 | Conrad | 426/28 |
| 4,374,860 | 2/1983 | Gasser | 426/28 |
| 4,447,532 | 5/1984 | Coker et al. | 435/99 |
| 4,710,386 | 12/1987 | Fulger et al. | 426/28 |
| 4,804,545 | 2/1989 | Goering et al. | 426/8 |
| 4,996,063 | 2/1991 | Inglett | 426/21 |
| 5,082,673 | 1/1992 | Inglett | 426/21 |
| 5,094,872 | 3/1992 | Furcsik et al. | 426/658 |

OTHER PUBLICATIONS

"Agricultural Inventions Catalog Supplement", USDA-ARS, Jun. 1990, pp. 123-124.
Inglett, G. E., "Action Pattern of *Bacillus Licheniformis* Alpha-Amylase On Ordinary, Waxy, and High-Amylose Corn Starches and Their Hydroxypropyl Derivatives", *Journal of Food Biochemistry*, 11(1987), pp. 249-258.
"Fat Replacer Cuts Calories In Fatty Foods", *Food Engineering*, Sep. 1981, p. 105.
Kaper, Fred S. et al., "Replace Oil And Fat with Potato-Based Ingredient", *Food Technology*, Mar. 1987, pp. 112-113.
Wood, P. J., "Physiological Effects of $\beta$-D-Glucan Rich Fractions from Oats", *Cereal Foods World*, vol. 34, No. 10 (Oct. 1989), pp. 878-882.

Primary Examiner—Jeanette Hunter
Attorney, Agent, or Firm—M. Howard Silverstein; Curtis P. Ribando; John D. Fado

[57] ABSTRACT

Amylodextrin compositions are produced from starch hydrolysates having a dextrose equivalent (DE) less than 10 or from milled substrates such as cereals, oilseeds, and vegetable fibers. The compositions give aqueous gels with unexpectedly increased strengths and improved fat-sparing characteristics, including more desirable flavor and texture qualities. The amylodextrin compositions are segregated from hydrolyzed aqueous cereal flour or starch hydrolysate solutions, for example, by precipitation with the proper amount of a water-miscible organic solvent, such as ethanol, acetone, or 2-propanol.

28 Claims, No Drawings

AMYLODEXTRIN COMPOSITIONS AND METHOD THEREFOR

BACKGROUND OF THE INVENTION

Dietary fiber is considered to be the soluble and insoluble components of food that are not digested by enzymes in the human gastrointestinal tract. The primary sources of dietary fiber include such cell wall materials as cellulose, hemicelluloses, lignin and pectins, along with gums and mucilages. Dietary fiber has been considered an important food component since early times. Recently, Burkitt et al. [Lancet 2: 1408-11411 (1972)] concluded that dietary fiber has a role in the prevention of certain large-intestine diseases, including cancer of the colon and diverticulitis. Diets containing large amounts of dietary fiber lead to stools that are softer and larger, and bowel movements are generally more frequent. Burkitt also mentioned that the serum cholesterol rises when dietary fiber is removed from the diet, and that eating a fiber-rich diet lowers serum cholesterol. Trowell [Am. J. Clin. Nutr. 25: 4644-465 (1972)] reached a similar conclusion regarding the relationship between fiber and health benefits.

It is now known that all dietary fiber is not the same and that different fibers provide different health benefits. For example, wheat bran is very rich in insoluble dietary fiber (mainly cellulose and hemicelluloses) and is excellent for decreasing the transit time of food through the digestive tract [Anderson et al., Am. J. Clin. Nutr. 32: 346-363 (1979)]. Some fibers are reported to reduce total plasma cholesterol [Munoz et al., Am. J. Clin. Nutr. 32: 580-592 (1979)].

This invention relates to a novel food composition from a cereal flour that provides soluble fiber useful as a functionally and nutritionally advantageous ingredient for a variety of food products.

DESCRIPTION OF THE PRIOR ART

The first indication of serum cholesterol lowering by roller oats was observed in rats by Degroot et al. [Lancet 2: 303-304 (1963)]. Fisher et al. [Proc. Soc. Exp. Biol. Med. 126: 108-111 (1967)] reported that the fiber fraction of oats is responsible for its unique effects on cholesterol. Over the years, numerous experiments with animals have shown that oat fiber has a strong hypocholesterolemic effect. Anderson et al. [Am. J. Clin. Nutr. 34: 824-829 (1981); 40: 1146-1155 (1984)] have confirmed hypocholesterolemic effects of oats in humans.

It is the soluble fiber that is effective in lowering cholesterol levels. Oatmeal, or rolled oats, and especially oat bran are the best sources of this soluble fiber. Moreover, oat fiber reduces the amount of low density lipoprotein (LDL) without lowering the beneficial high density lipoprotein (HDL). In fact, Anderson et al. [66th Annual Meeting, Am. Assoc. Cer. Chemists, Abstract No. 112 (1981)] teach that oat bran fed to humans can reduce LDL 58% while increasing HDL 82%. Other water-soluble fibers, such as pectin and guar gum, can lower serum cholesterol, but they are frequently accompanied by undesirable side effects such as nausea and vomiting. The results of another study by Anderson et al. (supra, 1984) indicate that oat bran diets decrease total serum cholesterol 19% and LDL 23%, and the oat bran increases bile acid excretion 65%. These studies clearly document hypocholesterolemic effects in humans of oat products which are rich in soluble fiber.

In the art of starch hydrolysis, it is known that starch can be hydrolyzed by acids or enzymes to give a variety of products, with properties depending on the degree of conversion. Acid conversions are known to give uniform distribution of hydrolysate fragments because of random cleavages of the starch molecule, whereas enzymes result in variations in amounts of the different oligomer fragments [Inglett, J. Food Biochem. 11: 249-258 (1987)]. Various amylolytic enzymes are used in the thinning or liquefaction of starch and in the production of low conversion starch hydrolysates which are known in the trade as maltodextrins or corn syrup solids, depending upon the degree of hydrolysis (Morehouse, U.S. Pat. No. 3,663,369). It is also recognized that specific maltodextrins can be prepared at a Dextrose Equivalent (D.E.) within the range of 10-13 (Coker, U.S. Pat. No. 4,447,532). The starches used to prepare maltodextrins are obtained primarily from the wet milling of corn. Other sources of starch for commercial products are tapioca, potato, and rice.

Whole cereal flours have also been subjected to starch-hydrolyzing conditions and have yielded, for example, a whole-grain hydrolyzed product (Conrad, U.S. Pat. No. 4,377,602) and a ready-to-eat, enzyme saccharified cereal (Fulger et al., U.S. Pat. No. 4,710,386). Ronai (U.S. Pat. No. 3,640,729) arrives at a similar product by adding prehydrolyzed starch to oat flour to yield an instant oat cereal product.

More recently U.S. Pat. No. 4,996,063 (which is hereby incorporated by reference) describes the preparation of a soluble dietary fiber composition by treating an aqueous dispersion of a gelatinized, milled, oat substrate with an α-amylase under conditions which hydrolyze the substrate to yield soluble and insoluble fractions. The soluble fraction is separated from the insoluble fraction, and water-soluble dietary fiber—substantially free of water-insoluble fiber—is recovered from the soluble fraction. The recovered water-soluble dietary fiber compositions have desirable color and flavor characteristics and are suitable for use in a variety of foods.

Thus although there are a variety of known dietary fiber products, the need in this field of art for improved dietary fiber products and processes for producing dietary fiber products persists.

SUMMARY OF THE INVENTION

This invention is directed to a process for preparing water-soluble, high molecular weight, amylodextrin compositions, having desirable flavor, texture, gel strength and improved fat-sparing characteristics, from starch hydrolysates having a DE of less than about 10 or from finely milled substrates. I have unexpectedly discovered that the amylodextrin compositions formed in accordance with the invention possess higher gel strengths.

One process comprises treating an aqueous dispersion of a finely milled substrate with an α-amylase under conditions which will hydrolyze the substrate and yield a soluble fraction and an insoluble fraction; separating the soluble fraction from the insoluble fraction; and fractionating or recovering the amylodextrin compositions from the water-soluble fraction such as by precipitation with a water-miscible organic solvent.

In another aspect of this invention the amylodextrin compositions are prepared from starch hydrolysates by preparing an aqueous solution of the starch hydrolysate and fractionating the amylodextrin compositions from the aqueous solution.

Yet other aspects of this invention are directed to amylodextrin compositions made by the above described processes and to foodstuffs prepared therefrom.

Other objects and advantages of this invention will become readily apparent from the ensuing description.

DETAILED DESCRIPTION OF THE INVENTION

Suitable substrates contemplated for use in the invention include finely milled cereals, oilseeds and vegetable fibers such as oat, oat bran, barley, barley bran, rice, rice bran, wheat, wheat bran, soy, pea and psyllium husk flours and sugar beet fiber. For those cereal substrates (e.g., wheat bran) that are not typically thought of as being in a finely milled form (i.e., flour), the term finely milled cereal substrate is intended to include the milled (i.e., flour form) of the cereal. The flour form (i.e., small particles) of the cereal facilitates the hydrolysis. When milled oilseeds and vegetable fibers are employed as the substrate, starch may be added prior to treatment.

According to an associated aspect of this invention, in the alternative to hydrolyzed food starches such as those starches isolated from the above milled cereals and subsequently hydrolyzed through the action of α-amylase, other hydrolyzed food starches (e.g., corn, potato, tapioca, wheat), dextrins or maltodextrins may be used in the fractionation step described below. These hydrolyzed food starches may be prepared through a variety of procedures such as the action of α-amylase (as described below) or conventional acid hydrolysis or combinations thereof.

The finely milled substrate is slurried in a sufficient amount of water to give a concentration in the range of about 10-40% by weight. The water preferably contains a suitable calcium salt in an amount sufficient to stabilize the subsequently added α-amylase [preferably about 25-50 parts per million (ppm) of calcium]. The slurried substrate may be gelatinized prior to enzymatic treatment, using any method known in the art. The pH of the ungelatinized slurry or the gelatinized dispersion is adjusted to about 5.5-7.5, preferably about 6.0, with sodium hydroxide or other alkali, and the α-amylase is added. If ungelatinized slurried substrate is initially employed, rapid hydrolysis by the α-amylase and gelatinization of the substrate will occur when the substrate is heated to a gelatinization temperature.

It is advantageous to use thermostable α-amylases referred to as 1,4-α-D-glucan glucanohydrolases and having the essential enzymatic characteristics of those produced by *Bacillus stearothermophilus*, strains ATCC Nos. 31,195; 31,196; 31,197; 31,198; 31,199; and 31,783. These strains are described in U.S. Pat. No. 4,284,722, which is herein incorporated by reference. Other sources of this enzyme include organisms such as *B. subtilis* which have been genetically modified to express the thermostable α-amylase of *B. stearothermophilus* as described in U.S. Pat. No. 4,493,893, herein incorporated by reference. These enzymes are available commercially under the name "G-Zyme G995" (formerly "Enzeco Thermolase," Enzyme Development Div., Biddle Sawyer Corp., New York, N.Y.).

Other suitable α-amylases are those having the essential enzymatic characteristics of those produced by *B. licheniformis* var. as described in U.S. Pat. Nos. 4,717,662 and 4,724,208, herein incorporated by reference. These enzymes are available commercially under the name "Taka-lite" (Solvay Enzymes Inc., Elkhart, Ind.). Of course, any α-amylase which is useful in the thinning of the cereal product is contemplated for use herein.

The conditions of enzyme treatment, including the enzyme concentration and the time and temperature of reaction, are selected to achieve liquefaction of the starch in the substrate to the extent that the soluble fiber bound by the cellular matrix is substantially completely liberated into solution. When using a thermostable α-amylase, a preferred treatment temperature is in the range of about 60°-100° C., preferably about 95° C. At these temperatures, gelatinization of the starch in the substrate occurs concurrently with the hydrolysis. The duration of the treatment at the desired conversion temperature depends on the desired product properties. Typically, the treatment period should be sufficient to result in a starch hydrolysate having a DE of less than about 10. Generally this ranges from about 1-10 min.

After completion of the enzymatic hydrolysis, the enzyme is inactivated, such as by passing the mixture through a steam injection pressure cooker at a temperature of about 140° C. Alternatively, the enzyme may be inactivated by acidification (pH 3.5-4.0) at 95° C., for about 10 min. Optional neutralization with alkali increases the salt concentration of the product.

After the enzyme has been inactivated (or following acid hydrolysis of food starches such as corn, potato, etc.), the soluble fraction comprising the soluble fiber and maltooligosaccharides is separated from the insoluble residue by a suitable method such as filtration or centrifugation.

The amylodextrin composition is then fractionated or separated from the water-soluble fraction. In accordance with the preferred embodiment, fractionation of the amylodextrin composition from the water-soluble fraction is accomplished by precipitation. The pH of the soluble fraction to be treated is again adjusted to about 5.5-7.5, preferably about 6.0, with sodium hydroxide or other alkali. Activated carbon may be added to facilitate purification, followed by filtration. Then enough water-miscible organic solvent sufficient to precipitate the desired amylodextrin composition is added to the soluble fraction. The precipitate is separated by, for example, filtration from the mixture and, if desired, dried. The practitioner skilled in the art will recognize that other techniques may be employed for fractionating the amylodextrin composition from the soluble fraction. Such alternatives include but are not limited to chromatography (e.g., size exclusion chromatography) or adsorption.

Any water-miscible organic solvent that successfully precipitates the desired amylodextrin compositions from the water-soluble fraction may be used. However, it is preferred to use a water-miscible organic solvent that has a dielectric constant greater than about 18, preferably having oxygen as the only heteroatom. Preferred solvents include ethanol, 2-propanol and acetone. It is especially preferred to use ethanol.

The amylodextrin precipitate produced by the process of this invention is a substantially pure water-soluble, high molecular weight amylodextrin composition. The term substantially pure composition is meant to encompass other minor components (e.g., starch, glucose, maltose, maltotriose) that may remain in the precipitate, although typically these comprise less than 10%. The degree of polymerization (DP) varies with the starting material, but the alcohol precipitate has an increased DP in comparison to the total water-soluble fraction. (See Example 7 and Table II.) Preferably the DP is from about 1.5 to about 4 times that of the unfractionated compositions. An increased DP is believed to contribute to improved aqueous gel strength and hedonic attributes.

The products produced by the process of this invention are adapted for use as functional and nutritional components of many foods such as dairy products, dairy product substitutes, meats, high-soluble fiber bakery products, frozen foods, yogurt, snacks, confectioneries, coatings, dietary-fiber beverages, and breakfast foods. These are prepared from the amylodextrin compositions by conventional methods.

This invention provides a process for making water-soluble dietary fiber having improved qualities; specifically, the amylodextrin compositions produced by this process exhibit greatly increased gel strength in comparison with the soluble fraction, less flavor, and texture and fat-sparing characteristics. By fat-sparing characteristics is meant compositions that can be used as aqueous gels to replace a significant part of the fat in a recipe (e.g., milkfat in ice cream, whipped cream, cheese) to give a lower calorie product with comparable taste and mouth feel.

The following examples are presented only to further illustrate the invention and are not intended to limit the scope of the invention, which is defined by the claims.

All percentages herein disclosed are by weight unless otherwise specified.

EXAMPLE 1

Six kilograms of oat bran flour (Quaker Oats Company) was dispersed in 34 L of water containing 50 ppm of calcium (0.185 g/L $CaCl_2.2H_2O$) in a 30-gallon kettle. The pH of the slurry was adjusted from 5.77 to 6.02 with 1.0N NaOH. After gelatinization by passage of the mixture through a steam injection jet cooker, the slurry was collected in a 30-gallon steam-jacketed kettle. When the temperature reached 90°-94° C., 14.4 mL of "Taka-lite L-340" $\alpha$-amylase enzyme (Solvay Enzymes, Inc., Elkhart, Ind.) was added to the mixture, giving a concentration of 816 Modified Wohlgemuth Units (MWU) per gram of substrate, where 1 MWU is that activity which will dextrinize 1 mg of soluble starch to a defined size dextrin in 30 min under specified conditions. After 2 min the pH was adjusted to 4.0 with 1.0N HCl. The mixture was heated for another 10 min, keeping the pH near 4.0 by periodic addition of 1.0N HCl, then cooled to 39°-42° C. by addition of 15-20 kg distilled water ice and centrifuged at 15,000 rpm in a large "Sharples" centrifuge to separate the insoluble components. The supernate was adjusted to pH 6.0 with 1.0N NaOH, 300 g of activated carbon (DARCO, 12-20 mesh) was added with slow mixing for 30 min and filtered off through cheesecloth. The liquid was stored for 16 hr at 1° C., then centrifuged at low speed in the "Sharples." The 5.79 kg combined wet solids from the two centrifuge steps was freeze-dried, yielding 1908 g of insolubles (32%). The supernate (63.4 L) was transferred to a 30-gallon container and 63.4 L of 95% ethanol was added with stirring. The mixture was allowed to stand overnight at room temperature and then decanted. The precipitated material was filtered in a large stainless steel suction flask, repulped with absolute ethanol for several minutes and filtered. The solid was air-dried at 40° C. for 2-3 days, yielding 1693 g (28%) of amylodextrin composition.

EXAMPLE 2

Four kilograms of whole oat flour (National Oats Company) was dispersed in 16 L of water containing 50 ppm of calcium (0.185 g/L $CaCl_2.2H_2O$) in a 30-gallon kettle. The pH of the slurry was adjusted from 5.54 to 5.99 with 1.0N NaOH. After gelatinization by passage of the mixture through a steam injection jet-cooler, the slurry was collected in a 30-gallon steam-jacketed kettle. When the temperature reached 90°-94° C., 2.4 mL of "Taka-lite L-340" (vide supra) was added to the mixture, giving a concentration of 204 MWU/g substrate. After 2 min the pH was adjusted to 4.0 with 1.0N HCl. The mixture was heated at 90°-94° C. for another 10 min. The pH was kept near 4.0 by periodic addition of 1.0N HCl, then the mixture was cooled to 68° C. by standing and centrifuged at 15,000 rpm in a large "Sharples" centrifuge to separate the insoluble components. The 2.15 kg wet solids was freeze-dried, yielding 660 g of insolubles (16%). The supernate (16 L) was adjusted to pH 6.1 with 1.0NaOH, transferred to a 30-gallon container, and 16 L of 95% ethanol was added with stirring. The mixture was allowed to stand overnight at room temperature and then decanted. The precipitated material was repulped with 2.8 L of absolute ethanol for several minutes and filtered. The solid was air-dried, yielding 2556 g (64%) of amylodextrin material.

EXAMPLE 3

Four kilograms of potato dextrin ("Paselli SA2," AVEBE America Inc., Princeton, N.J.) was dispersed in 16 L of water in a 30-gallon steam jacketed kettle; the pH of the slurry was 6.00. The mixture was heated until a clear solution was formed (about 78° C.), then cooled to 50° C. by standing. To the 18 L of solution was added 18 L of 95% ethanol with stirring. The mixture was allowed to stand overnight at room temperature and then decanted. The precipitated material was twice repulped with 2.8 L of absolute ethanol for several minutes and filtered. The solid was air-dried at room temperature for 3 days yielding 3141 g (78%) of amylodextrin material.

EXAMPLE 4

Four kilograms of corn maltodextrin ("Maltrin M040", Grain Processing Co., Muscatine, Iowa) was dispersed in 16 L of water in a 30-gallon steam-jacketed kettle; the pH of the slurry was 4.6. The mixture was heated until a clear solution was formed (about 53° C.), then cooled to 50° C. by standing. To the 19 L of solution was added 19 L of 95% ethanol with stirring. The mixture was allowed to stand overnight at room temperature and then decanted. The precipitated material was twice repulped with 3.0 L of absolute ethanol for several minutes and filtered. The solid was air dried at room temperature for 3 days, yielding 2364 g (59%) of amylodextrin material.

EXAMPLE 5

Three hundred grams of tapioca dextrin ("Instant N-Oil II," National Starch and Chemical Co., Bridgewater, N.J.) was dispersed in 1200 mL of boiling water, stirred for 5 min and homogenized for 1 min. The mixture was cooled to 50°-60° C. by standing, and 1500 mL of absolute ethanol was added with stirring. The mixture was cooled to 5°-10° C. in a salt/ice bath and then decanted. The precipitated material was roll dried, yielding 247 g (82%) of amylodextrin material.

EXAMPLE 6

Aqueous gels were prepared from the recovered amylodextrin material of Examples 1–5 as follows: 125 g of solid was blended with 375 mL boiling nanopure water in a "Sorvall" homogenizer for one min. The mixture was transferred to a warmed 600 mL beaker, placed in a 77° C. water bath and stirred for 20 min at 75° C. The samples were then refrigerated for about a week at 4° C. Gel strengths were measured with a Precision Model 73510 Cone Penetrometer. The values given in Table I represent the depth of penetration (in tenths of millimeters) of a 150 g conical probe into the gel in 5 seconds. The amylodextrin gels all had lower penetration than the unfractionated amylodextrin gels, indicating greatly increased gel strength.

EXAMPLE 7

Number average molecular weight ($M_n$) of the amylodextrin compositions prepared herein were estimated by size exclusion chromatography. Results are given in Table II. System hardware and operating parameters:

| Pump: | "SpectraPhysics 8810" |
|---|---|
| Autosampler: | "SpectraPhysics 8780" |
| Detector: | "Waters 410 refractive index" (35° C.) |
| Integrator: | "SpectraPhysics 4270" |
| Column: | "Waters Linear Ultrahydrogel" (45° C.) |
| Mobile Phase: | Unbuffered nanopure water, 0.5 mL/min (149 psig) |
| Sample: | 20 μL loop injection, 5 g/L concentration |

In every case the amylodextrin had a significantly higher average molecular weight and degree of polymerization than its unfractionated substrate.

TABLE I

| | Penetrometer Gel Strengths of Amylodextrins | | |
|---|---|---|---|
| Amylodextrin | Gel % Solids | Unfractionated Amylodextrin | Amylodextrin Composition |
| Oat Bran, Ex. 1 | 25 | 500+ | 157 |
| Oat Flour, Ex. 2 | 25 | 500+ | 103 |
| Potato, Ex. 3 | 25 | 165 | 96 |
| Corn, Ex. 4 | 25 | 500+ | 299 |
| Tapioca, Ex. 5 | 20[a] | 187 | 174 |

[a]Insufficient material for 25% gel

TABLE II

| | Size Exclusion Chromatography of Amylodextrins | | | |
|---|---|---|---|---|
| Sample | Mean Retention Time | Molecular Weight $M_n$ | Degree of Polymerization | DP[a] Ratio |
| Dextrose | 22.69 min | 180 | 1 | |
| Dextran Std A | 17.69 min | 48,000 | 267 | |
| Dextran Std B | 14.81 min | 853,000[b] | 4740 | |
| Example 1 MAC | 16.73 min | 117,500 | 653 | 3.23 |
| Example 1 Unfr[c] | 17.82 min | 36,300 | 202 | |
| Example 3 MAC | 14.55 min | 1,230,000 | 6830 | 2.09 |
| Example 3 Unfr | 15.23 min | 589,000 | 3270 | |
| Example 4 MAC | 18.16 min | 25,100 | 139 | 3.16 |
| Example 4 Unfr | 19.23 min | 7,490 | 44 | |
| Example 5 MAC | 15.62 min | 389,000 | 2160 | 3.16 |
| Example 5 Unfr | 16.69 min | 123,000 | 683 | |

[a]Ratio of DP of precipitated amylodextrin to unfractionated amylodextrin.
[b]Calibration Curve: Log ($M_n$) = 12.909−0.4685 (avg min ret time); $r^2$ = 0.9992
[c]Sample corresponds to oat soluble dietary fiber from U.S. Pat. No. 4,996,063 - Example 9

EXAMPLES 8–9

Five kilogram batches of chocolate soft-serve frozen dessert were prepared with the amylodextrin compositions of Examples 1 and 5, as shown in Table III. All ingredients except the amylodextrins were mixed together, heated in a microwave oven and blended in an Oster Blender until homogeneous. Of this mixture, 1,000 mL was removed and the amylodextrins were added. The material was heated at 86° C. for 25 sec in the microwave oven, mixed with the remainder of the mixture in the blender, cooled to 4° C. in a refrigerator and then frozen in a Electro Freeze Model 22 soft-serve dessert freezer (H. C. Duke & Sons Inc., E. Moline, Ill.). A taste panel reported that the Example 8 dessert was creamy with strong chocolate flavor and no mouth coating or aftertaste, comparable to "Dairy Queen" of "Prairie Farms" chocolate ice milk. The Example 9 dessert was very creamy with good chocolate flavor, no mouth coating or aftertaste, but had a very dense consistency and wax-like coating.

It is understood that the foregoing detailed examples are given merely by way of illustration and that modification and variations may be made therein without departing from the spirit and scope of the invention.

TABLE III

| | Frozen Desserts Containing Amylodextrins | | | |
|---|---|---|---|---|
| | Example 8 | | Example 9 | |
| Ingredient | Grams | Wt % | Grams | Wt % |
| Skim milk | 3750 | 71.8 | 3750 | 71.8 |
| Non-fat milk solids | 300 | 5.7 | 300 | 5.7 |
| Cane sugar | 600 | 11.5 | 600 | 11.5 |
| Vanilla extract | 100 | 1.9 | 100 | 1.9 |
| Imitation vanilla | 50 | 1.0 | 50 | 1.0 |
| Cocoa powder | 50 | 1.0 | 50 | 1.0 |
| Artificial chocolate | 20 | 0.4 | 20 | 0.4 |
| Stabilizer | 50 | 1.0 | 50 | 1.0 |
| Example 5 amylodextrin | 100 | 1.9 | 100 | 1.9 |
| Example 1 amylodextrin | 200 | 3.8 | — | — |
| Dextrin composition[a] | — | — | 200 | 3.8 |

[a]Sample corresponds to oat soluble dietary fiber from U.S. Pat. No. 4,996,063 - Example 9

We claim:

1. A method for producing amylodextrin compositions, comprising treating an aqueous dispersion of a milled substrate selected from the group consisting of cereals, oilseeds, and vegetable fibers, with an α-amylase under conditions which will hydrolyze the substrate to liberate soluble fiber bound by the cellular matrix of the substrate into solution and yield a water-soluble fraction and a water-insoluble fraction, separating said water-soluble fraction from said water-insoluble fraction, and fractionating said amylodextrin compositions from said water-soluble fraction.

2. The method of claim 1 wherein said substrate is selected from the group consisting of oat, oat bran, barley, barley bran, rice, rice bran, wheat, wheat bran, soy, pea and psyllium husk flours and sugar beet fiber.

3. The method of claim 2 wherein said α-amylase is a thermostable α-amylase and said cereal substrate is gelatinized concurrently with said hydrolysis.

4. The method of claim 1 wherein said soluble fraction is separated from said insoluble fraction by centrifugation or filtration.

5. The method of claim 1 wherein said fractionating comprises precipitating said amylodextrin compositions from said soluble fraction with a water-miscible organic solvent.

6. The method of claim 5 wherein said water-miscible solvent has a dielectric constant greater than about 18.

7. The method of claim 5 wherein said water-miscible organic solvent is selected from the group consisting of ethanol, 2-propanol and acetone.

8. The method of claim 5 wherein said water-miscible organic solvent is ethanol.

9. A method for producing amylodextrin compositions comprising preparing an aqueous solution of a starch hydrolysate having a DE of less than 10 and fractionating said amylodextrin compositions from said aqueous solution.

10. The method of claim 9 wherein said starch hydrolysate is selected from the group consisting of corn, potato, tapioca, and wheat dextrins and maltodextrins.

11. The method of claim 9 wherein said fractionating comprises precipitating said amylodextrin compositions from said aqueous solution with a water-miscible organic solvent.

12. The method of claim 11 wherein said water-miscible organic solvent has a dielectric constant greater than about 18.

13. The method of claim 11 wherein said water-miscible organic solvent is selected from the group consisting of ethanol, 2-propanol and acetone.

14. The method of claim 11 wherein said water-miscible organic solvent is ethanol.

15. Amylodextrin compositions produced by the method of claim 1.

16. Amylodextrin compositions produced by the method of claim 2.

17. Amylodextrin compositions produced by the method of claim 3.

18. Amylodextrin compositions produced by the method of claim 4.

19. Amylodextrin compositions produced by the method of claim 5.

20. Amylodextrin compositions produced by the method of claim 6.

21. Amylodextrin compositions produced by the method of claim 7.

22. Amylodextrin compositions produced by the method of claim 9.

23. Amylodextrin compositions produced by the method of claim 10.

24. Amylodextrin compositions produced by the method of claim 11.

25. Amylodextrin compositions produced by the method of claim 12.

26. Amylodextrin compositions produced by the method of claim 13.

27. A foodstuff including the amylodextrin compositions of claim 1.

28. A foodstuff including the amylodextrin compositions of claim 9.

* * * * *